United States Patent [19]

Frisch et al.

[11] Patent Number: 5,518,991
[45] Date of Patent: May 21, 1996

[54] SUSPOEMULSIONS BASED ON FENOXAPROP-ETHYL

[75] Inventors: Gerhard Frisch, Wehrheim/Taunus; Thomas Maier, Frankfurt am Main, both of Germany

[73] Assignee: Hoechst Aktiengesellschaft, Frankfurt, Germany

[21] Appl. No.: 350,588

[22] Filed: Dec. 6, 1994

Related U.S. Application Data

[63] Continuation of Ser. No. 229,141, Apr. 18, 1994, abandoned, which is a continuation of Ser. No. 883,351, May 15, 1992, abandoned.

[30] Foreign Application Priority Data

May 18, 1991 [DE] Germany .................. 41 16 440.7

[51] Int. Cl.$^6$ ...................... A01N 43/76; A01N 47/30
[52] U.S. Cl. .................. 504/138; 504/116; 504/148; 71/DIG. 1
[58] Field of Search ........................ 504/116, 129, 504/138, 148

[56] References Cited

U.S. PATENT DOCUMENTS

| | | | |
|---|---|---|---|
| 4,870,103 | 9/1989 | Röechling et al. | 71/88 |
| 5,074,905 | 12/1991 | Frisch et al. | 71/120 |

FOREIGN PATENT DOCUMENTS

| | | |
|---|---|---|
| 0117999 | 9/1984 | European Pat. Off. . |
| 0261492 | 3/1988 | European Pat. Off. . |
| 0330904 | 9/1989 | European Pat. Off. . |
| 0400585 | 12/1990 | European Pat. Off. . |
| 3624910 | 1/1988 | Germany . |
| 2095112 | 9/1982 | United Kingdom . |
| WO91/06215 | 5/1991 | WIPO . |

*Primary Examiner*—Allen J. Robinson
*Assistant Examiner*—Brian Bembenick
*Attorney, Agent, or Firm*—Curtis, Morris & Safford

[57] ABSTRACT

The invention relates to storage-stable aqueous suspoemulsions which comprise fenoxaprop-ethyl, a sulfonylurea and/or phenylurea, an aromatic solvent and a surfactant combination of ethoxylated tristyrylphenol and ethoxylated synthesis alcohol, which are phosphated if appropriate, to processes for their preparation and to their use in plant protection.

12 Claims, No Drawings

SUSPOEMULSIONS BASED ON FENOXAPROP-ETHYL

This application is a continuation of application Ser. No. 08/229,141, filed Apr. 18, 1994 abandoned which in turn is a continuation of application Ser. No. 07/883,351, filed May 15, 1992 (abandoned).

The invention relates to suspoemulsions based on fenoxaprop-ethyl. Suspoemulsions (SE) of various types are described, for example, in EP-A-0117999, U.S. Pat. No. 4,824,663, EP-A-0289356, EP-A-0261492 and EP-A-0143099. A review of the latest art in the field of suspoemulsions is to be found on the one hand in Pestic. Sci. 1990, 29, 451–465 (Recent Development in Suspoemulsions, P. Mulqueen et al.) and on the other hand in Pestic. Sci. 1990, 29, 437–449 (Trends in the Formulation of Pesticides—An Overview, D. Seaman). It is furthermore known that a formulation depends very much on the active compounds contained therein. The influence of the active compounds then manifests itself quite decisively in the nature and composition of surfactants in these multiphase formulations. The corresponding solvent for the phase which is to be emulsified and in which one or more active compounds are dissolved also plays an important role here.

Already existing, known systems—such as, for example, those mentioned above—therefore cannot always be resorted to for the preparation of suspoemulsions of novel active compounds, such as, for example, fenoxaprop-ethyl, with representatives from the novel class of sulfonylureas, such as, for example, amidosulfuron, or the already known phenylurea derivatives, such as, for example, isoproturon. Fenoxaprop-ethyl thus does not have too good a solubility in phthalic acid esters (EP-A-0177999), while it has a very good solubility in aromatic solvents such as xylene or ethylbenzene, or in mixtures of aromatics, such as, for example, the solvents of the ®Solvesso series from Esso. Nevertheless, no particularly stable emulsion can be formed from fenoxaprop-ethyl in such solvents with block polymers (EP-A-0261492) or "graft copolymers" (EP-A-0289356 or GB Patent 2026341 A) in dispersion-containing water.

It has now been found, surprisingly, that storage-stable and technologically problem-free suspoemulsions of fenoxaprop-ethyl with herbicides from the sulfonylurea series, for example amidosulfuron, or from the phenylurea series, for example isoproturon, can be prepared with the aid of a certain solvent and surfactant combination. Moreover, in the case of amidosulfuron virtually no chemical degradation of the active compound is found, although this could be expected on the basis of the chemical structure. Phenylurea derivatives, such as isoproturon, are stable in aqueous dispersions. Safeners can also be added to these suspoemulsions. This also particularly applies to fenoxaprop-ethyl if, for example, it is dissolved in the organic phase in combination with the safener ethyl 1-(2,4-dichlorophenyl)-5-trichloromethyl-(1 H)-1,2,4-triazole-3-carboxylate (EP-A-0174562). No interactions which have adverse effects on the stability and action of the system take place between the safener and the fenoxaprop-ethyl in the system described.

The invention therefore relates to suspoemulsions which comprise fenoxaprop-ethyl, at least one herbicidal active compound from the sulfonylurea series and/or from the phenylurea series, an aromatic solvent or solvent mixture and a surfactant combination of ethoxylated tristyrylphenol and ethoxylated sterically modified synthesis alcohol of average chain length $C_{13}$, each of which can be phosphated and neutralized with alkali or amine.

Fenoxaprop-ethyl can be employed as a stereoisomer mixture (for example as the racemate) or in the form of the D(+)-isomer fenoxaprop-P-ethyl.

Possible herbicides from the sulfonylurea series are pyrimidine- or triazinylaminocarbonyl-[benzene-, pyridine-, pyrazole-, thiophene- and (alkylsulfonyl)-alkylamino-]-sulfamides. Preferred substituents on the pyrimidine ring or triazine ring are alkoxy, alkyl, haloalkoxy, haloalkyl, halogen or dimethylamino, it being possible for all the substituents to be combined independently of one another. Preferred substituents in the benzene, pyridine, pyrazole, thiophene or (alkylsulfonyl)alkylamino part are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl and (alkanesulfonyl)alkylamino.

Examples of suitable sulfonylureas are 1) phenyl- and benzylsulfonylureas and related compounds, for example 1-(2-chlorophenylsulfonyl)-3-(4-methoxy-6-methyl-1,3,5-triazin-2-yl)-urea (chlorsulfuron), 1-(2-ethoxycarbonylphenylsulfonyl)-3-(4-chloro-6-methoxypyrimidin-2-yl)-urea (chlorimuron-ethyl), 1-(2-methoxyphenylsulfonyl)-3-(4-methoxy-6-methyl-1,3,5-triazin-2-yl)-urea (metsulfuron-methyl), 1-(2-chloroethoxy-phenylsulfonyl)-3-(4-methoxy-6-methyl-1,3,5-triazin-2-yl)-urea (triasulfuron), 1-(2-methoxycarbonyl-phenylsulfonyl)-3-(4,6-dimethylpyrimidin-2-yl)-urea (sulfometuron-methyl), 1-(2-methoxycarbonylphenylsulfonyl)-3-(4-methoxy-6-methyl-1,3,5-triazin-2-yl)-3-methylurea (tribenuronmethyl)

1-(2-methoxycarbonylbenzylsulfonyl)-3-(4,6-dimethoxypyrimidin-2-yl)-urea (bensulfuron-methyl)

1-(2-methoxycarbonylphenylsulfonyl)-3-(4,6-bis-(difluoromethoxy)-pyrimidin-2-yl)-urea (primisulfuron-methyl), 3-(4-ethyl-6-methoxy-1,3,5-triazin-2-yl)-1-(2,3-dihydro-1,1-dioxo-2-methylbenzo[b]thiophene-7-sulfonyl)-urea (see EP-A-79683) and 3-(4-ethoxy-6-ethyl-1,3,5-triazin-2-yl)-1-(2,3-dihydro-1,1-dioxo-2-methylbenzo[b]thiophene-7-sulfonyl)-urea (see EP-A-79683), 2) thienylsulfonylureas, for example 1-(2-methoxycarbonylthiophen-3-yl)-3-(4-methoxy-6-methyl-1,3,5-triazin-2-yl)-urea (thifensulfuron-methyl), 3) pyrazolylsulfonylureas, for example 1-(4-ethoxycarbonyl-1-methylpyrazol-5-yl-sulfonyl)-3-(4,6-dimethoxypyrimidin-2-yl)-urea (pyrazosulfuronmethyl) and methyl 3-chloro-5-(4,6-dimethoxypyrimidin-2-ylcarbamoylsulfamoyl)-1-methyl-pyrazole-4-carboxylate (see EP-A-282613), 4) sulfonyldiamide derivatives, for example 3-(4,6-dimethoxypyrimidin-2-yl)-1-(N-methyl-N-methylsulfonylaminosulfonyl)-urea (amidosulfuron) and structural analogs (see EP-A-0131258 and Z. Pfl. Krankh. Pfl. Schutz, Special Edition XII, 489–497 (1990)), 5) pyridylsulfonylureas, for example 1-(3-N,N-dimethylaminocarbonylpyridin-2-yl-sulfonyl)-3-(4,6-dimethoxypyrimidin-2-yl)-urea (nicosulfuron), 1-(3-ethylsulfonylpyridin-2-yl-sulfonyl)-3-(4,6-dimethoxypyrimidin-2-yl)-urea (DPX-E 9636, see Brighton Crop Prot. Conf.—Weeds—1989, page 23 et seq.) and pyridylsulfonylureas such as are described in German Patent Applications P 4000503.8 (HOE 90/F 006) and P 4030577.5 (HOE 90/F 293), preferably those of the formula I or salts thereof,

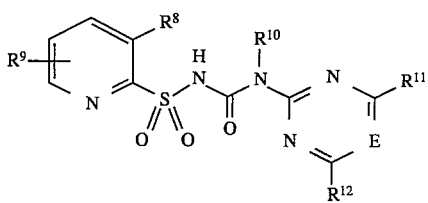

in which

E is CH or N, preferably CH, $R^8$ is iodine or $NR^{13}R^{14}$, $R^9$ is hydrogen, halogen, cyano, $(C_1-C_3)$-alkyl, $(C_1-C_3)$-alkoxy, $(C_1-C_3)$-haloalkyl, $(C_1-C_3)$-haloalkoxy, $(C_1-C_3)$-alkylmercapto, $(C_1-C_3)$-alkoxy-$(C_1-C_3)$-alkyl, $(C_1-C_3)$-alkoxy-carbonyl, mono- or di-$(C_1-C_3)$-alkylamino, $(C_1-C_3)$-alkyl-sulfinyl or -sulfonyl, $SO_2$—$NR^aR^b$ or CO—$NR^aR^b$, in particular H, $R^a$ and $R^b$ independently of one another are hydrogen, $(C_1-C_3)$-alkyl, $(C_1-C_3)$-alkenyl, $(C_1-C_3)$-alkynyl or together —$(CH_2)_4$—, —$(CH_2)_5$— or $(CH_2)_2$—O—$(CH_2)_2$—, $R^{10}$ is H or $CH_3$, $R^{11}$ is halogen, $(C_1-C_2)$-alkyl, $(C_1-C_2)$-alkoxy, $(C_1-C_2)$haloalkyl, preferably $CF_3$, or $(C_1-C_2)$-haloalkoxy, preferably $OCHF_2$ or $OCH_2CF_3$, $R^{12}$ is $(C_1-C_2)$-alkyl, $(C_1-C_2)$-haloalkoxy, preferably $OCHF_2$, or $(C_1-C_2)$-alkoxy and $R^{13}$ is $(C_1-C_4)$-alkyl and $R^{14}$ is $(C_1-C_4)$-alkylsulfonyl, or $R^{13}$ and $R^{14}$ together are a chain of the formula —$(CH_2)_3SO_2$— or —$(CH_2)_4SO_2$—, for example 3-(4,6-dimethoxypyrimidin-2-yl)-1-(3-N-methylsulfonyl-N-methylaminopyridin-2-yl)-sulfonylurea, and 6) alkoxyphenoxysulfonylureas such as are described in EP-A-0342569, preferably those of the formula II or salts thereof,

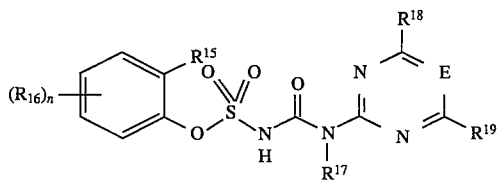

in which

E is CH or N, preferably CH, $R^{15}$ is ethoxy, propoxy or isopropoxy, $R^{16}$ is hydrogen, halogen, nitro, $CF_3$, CN, $(C_1-C_4)$-alkyl, $(C_1-C_4)$-alkoxy, $(C_1-C_4)$-alkylmercapto or $(C_1-C_3)$-alkoxy-carbonyl, preferably in the 6-position on the phenyl ring, n is 1, 2 or 3, preferably 1, $R^{17}$ is hydrogen, $(C_1-C_4)$-alkyl or $(C_3-C_4)$-alkenyl, $R^{18}$ and $R^{19}$ independently of one another are halogen, $(C_1-C_2)$-alkyl, $(C_1-C_2)$-alkoxy, $(C_1-C_2)$-haloalkyl, $(C_1-C_2)$-haloalkoxy or $(C_1-C_2)$-alkoxy-$(C_1-C_2)$-alkyl, preferably $OCH_3$ or $CH_3$, for example 3-(4,6-dimethoxypyrimidin-2-yl)-1-(2-ethoxyphenoxy)-sulfonylurea, and other related sulfonylurea derivatives and mixtures thereof. Amidosulfuron and/or isoproturon are preferred.

Examples of suitable phenylurea derivatives are isoproturon, diuron, chlortoluron, monolinuron, linuron, neburon, monuron, fluometuron, fenuron, siduron, terbuthuron, chlorbromuron and tetrafluoron.

The content of fenoxaprop-ethyl is preferably 0.1 to 20% by weight, in particular 0.2 to 10% by weight.

The content of sulfonylurea derivatives and/or phenylurea derivatives, preferably of sulfonyldiamide derivatives or isoproturon, is in general preferably 0.1 to 60% by weight, in particular 1 to 45% by weight, amidosulfuron in particular also being employed in somewhat smaller amounts (preferably 0.1 to 30% by weight, in particular 0.2 to 15% by weight).

Possible preferred solvent combinations are aromatic solvents which are derived from benzene, such as xylene, mesitylene, indane, diisopropylbenzene and higher homologs, as well as solvents from the ®Solvesso series from Esso or a mixture of the solvents mentioned. A naturally occurring oil of animal or vegetable origin is preferably added to these solvents or solvent mixtures, it being possible for the ratio of oil to aromatic to be 1:1 to 1:100, but preferably 1:4 to 1:50. The addition of naturally occurring oils not only brings about an improvement in the shear stability of the system, which is essential for preparation and storage, but can also additionally increase the penetration properties. The addition of a vegetable oil, such as rapeseed oil, is preferred. The total solvent content is preferably 2 to 70% by weight, in particular 3 to 50% by weight.

A possible surfactant mixture according to the invention is a combination of ethoxylated tristyrylphenols and ethoxylated, sterically modified synthesis alcohol of average chain length $C_{13}$ (isotridecyl alcohol), which can also be phosphated and neutralized with alkali or amines. 0.1 to 30% by weight, preferably 0.5 to 20% by weight, of the surfactant mixture is added. The degree of ethoxylation in the case of the tristyrylphenol derivatives can be between 10 and 40, but preferably between 14 and 28. The degree of ethoxylation of the isotridecyl alcohol can be between 2 and 20, preferably between 4 and 14. The tristyrylphenol derivatives are marketed, for example, under the trade names ®Soprophor BSU, ®Soprophor 3D33, ®Soprophor FL, ®Soprophor CY/8, ®Soprophor S/25, ®Soprophor FL/60, ®Soprophor FLK (Rhone Poulenc), Hoe S 3474, Hoe S 3475 and Hoe S 3775; the isotridecyl alcohol derivatives are from the ®Genapol X series (Hoechst). The ratio of ethoxylated tristyrylphenol derivatives to ethoxylated isotridecyl alcohol derivatives is 25:1 to 1:35, preferably 4:1 to 1:8.

Formulations which contain only tristyrylphenol derivatives, that is to say not the surfactant mixture according to the invention, are not stable to shear in the present case and have a marked tendency to agglomerate (see examples).

Another unexpected advantage is that this surfactant combination is accompanied by a significant improvement in the biological action. Experiments have shown (Table II) that, for example in the case of the combination isoproturon:fenoxaprop-ethyl, formulations with the above surfactant mixture were significantly better than comparable tank mixtures with the commercially available individual formulations or if, for example, ethoxylated isotridecyl alcohol was replaced by similar wetting agents, such as ®Genapol LRO.

The formulations according to the invention can comprise a dodecyl- or tridecylbenzenesulfonate in an amount of 0.01–12% by weight as an additional surfactant which helps to improve the properties of dispersal of the stably suspended particle but is not essential. Thus, for example, ®Maranil (dodecylbenzenesulfonate Na salt) from Henkel can be employed as a paste or powder.

Possible additional surfactants are furthermore those polyacrylic acid derivatives such as can be obtained, for example, under the trade names ®Sokalan CP10 (BASF), the ®Geropon series (HB, DA, DG) (Rhone Poulenc) or the ®Dispersant series (Rhone Poulenc) or the ®Degapas series (Degussa).

®Sokalan CP10 is a modified Na polyacrylate of low molecular weight, which is prepared by a special polymerization process (BASF Techn. Info TI/P 3039 d of 1988.).

The ®Geropon types HB, DA and DG and ®Dispersant HB and FB are, according to the Rhone-Poulenc data sheet of 1979 and 1989, alkali metal polyacrylates which are available both in liquid and in solid form.

The ®Degapas series are also alkali metal or ammonium salts of polyacrylic acid derivatives.

Up to 25% by weight, preferably up to 15% by weight, of commercially available auxiliaries, such as wetting agents, dispersing agents, foam suppressants, thickeners, preservatives and antifreeze agents, can furthermore also additionally be added.

Examples of possible additional wetting and dispersing agents are tributylphenol polyglycol ethers, such as the ®Sapogenat T brands (Hoechst) or nonylphenol polyglycol ethers, such as the ®Arkopal N brands (Hoechst).

Suitable foam suppressants are, for example, those based on silicone, such as those from the ®Silcolapse series (Rhone Poulenc), SE 39 or antifoam agent SH (Wacker).

Thickeners can be inorganic or organic in nature; they can also be combined. Suitable thickeners are, for example, those based on aluminum, xanthan, methylcellulose, polysaccharide, alkaline earth metal silicate, gelatine and polyvinyl alcohol, such as, for example, ®Bentone EW, ®Veegum, ®Rhodopol 23 or ®Kelzan S.

If necessary, preservatives are used, for example those based on formaldehyde, benzoic acid and triphenyltin, such as, for example, ®Kobate C.

Antifreeze agents, such as urea, salts, polyols (for example glycol, propylene glycol or glycerol) or sugars, can furthermore also be added.

The invention furthermore relates to a method of combating undesirable plant growth, which comprises applying a formulation according to the invention to plants, plant seeds or the cultivation area.

Suspoemulsions according to the invention are advantageously prepared from the individual dispersions of the dispersed active compounds, such as are used, for example, in the case of the phenylurea derivatives, such as, for example, linuron, isoproturon, diuron and chlortoluron and mixtures thereof. The active compounds are employed as finished formulations with the customary formulation auxiliaries, such as are described, for example, in EP-A-0022925, EP-A-0110174 and German Patent Application P 3538247.3. The suspoemulsion can be mixed intimately by, for example, wet grinding.

Aqueous dispersions are similarly also used as starting substances in the case of the sulfonylurea derivatives, such as, for example, amidosulfuron, as has been proposed in German Patent Application P 4116441.5. The aqueous dispersion phase can be brought together with the organic active compound solution phase, for example, in accordance with EP-A-0130370.

The weight ratio of aqueous to organic phase can be 1:1.5 to 50:1, but preferably 1:1 to 35:1.

Examples of the novel suspoemulsions according to the invention are listed in the following Tables I a and I b, without the invention being limited thereto.

TABLE Ia

| Example | 1 | 2 | 3 | 4 | 5 | 6 | 7 | 8 | 9 | 10 | 11 | 12 | 13 |
|---|---|---|---|---|---|---|---|---|---|---|---|---|---|
| Isoproturon (500 g/l) | 81.0 | 48.0 | 61.2 | 61.2 | 61.2 | 61.2 | 61.2 | 61.2 | 61.2 | 61.2 | 61.2 | 77.72 | 77.72 |
| Fenoxaprop-P-ethyl | 3.0 | 1.8 | 2.25 | 2.25 | 2.25 | 2.25 | 2.25 | 2.25 | 2.25 | 2.25 | 2.25 | 1.77 | 1.77 |
| Safener[1] | 1.7 | 1.02 | 1.28 | 1.28 | 1.28 | 1.28 | 1.28 | 1.28 | 1.28 | 1.28 | 1.28 | 0.93 | 0.93 |
| ® Genapol X060 | 0.5 | 0.9 | 1.27 | 1.2 | 2.0 | 2.5 | 5.0 | 7.5 | 10.0 | 5.0 | 4.0 | — | — |
| ® Soprophor FL | 2.0 | 4.0 | 3.0 | 6.0 | 3.0 | 2.5 | 2.5 | 2.5 | 2.5 | 3.0 | — | 2.0 | 2.0 |
| Rapeseed oil | 2.0 | 4.0 | 3.0 | 6.0 | 11.0 | 2.5 | 2.5 | 2.5 | 2.5 | 3.0 | 2.0 | 2.0 | — |
| ® Solvesso 150 | 9.8 | 40.28 | 28.0 | 22.07 | 19.27 | 20.0 | 17.5 | 15.0 | 12.5 | 24.27 | 23.0 | 15.58 | 17.58 |
| Hoe S 3475 | | | | | | | | | | | 3.0 | destroyed after shearing 4 × | destroyed after shearing 2 × |
| Water to 100% | | | | | | | | | | | | | |

TABLE Ib

| Example | 14 | 15 | 16 | 17 | 18 | 19 | 20 | 21 | 22 | 23 |
|---|---|---|---|---|---|---|---|---|---|---|
| Amidosulfuron | 3.26 | 3.26 | 3.23 | 3.4 | 3.6 | 3.2 | 3.2 | 3.2 | 3.5 | 3.5 |
| Fenoxaprop-P-ethyl | 7.13 | 7.13 | 7.06 | 7.3 | 6.92 | 6.92 | 7.0 | 7.0 | 8.0 | 8.0 |
| Safener[1] | | | | | 3.06 | 3.06 | 3.1 | 3.1 | 3.7 | 3.7 |
| ® Solvesso 150 | 32.87 | 32.87 | 32.94 | 33.43 | 22.02 | 22.0 | 22.0 | 22.0 | 25.5 | 25.5 |
| Rapeseed oil | 5.0 | 5.0 | 5.0 | 5.0 | 4.0 | 4.0 | 4.0 | 4.0 | 4.0 | 4.0 |
| ® Soprophor BSU | 5.0 | 5.0 | | | 4.0 | | | 4.0 | | |
| ® Soprophor FL | | | 5.0 | | | 4.0 | 4.0 | | | 4.0 |
| Hoe S 3474 | | | | 5.0 | | | | | 4.5 | |
| ® Sokalan CP10 | 1.27 | 1.27 | 1.27 | 1.3 | 1.3 | 1.3 | 1.3 | 1.3 | 1.5 | 1.7 |
| Glycerol | 1.0 | 2.0 | 1.0 | 1.02 | 1.0 | 1.0 | 2.0 | 1.0 | 2.0 | 1.0 |
| ® Maranil A | 0.25 | 0.5 | 0.5 | 0.5 | 0.5 | 0.25 | 0.5 | 0.25 | 0.25 | 0.5 |
| ® Darvan No. 3 | 0.127 | 0.127 | 0.13 | 0.13 | 0.13 | 0.13 | 0.13 | 0.13 | 0.13 | 0.13 |
| SE 39 | 0.127 | 0.127 | 0.13 | 0.13 | 0.13 | 0.13 | 0.13 | 0.13 | 0.13 | 0.13 |
| ® Silcolapse 5020 | 0.127 | 0.127 | 0.127 | 0.127 | 0.127 | 0.13 | 0.13 | 0.13 | 0.13 | 0.13 |
| ® Rhodopol 23 | 0.025 | 0.025 | 0.025 | 0.025 | 0.025 | 0.025 | 0.03 | 0.025 | 0.025 | 0.025 |
| ® Kobate C | 0.013 | 0.013 | 0.013 | 0.013 | 0.013 | 0.013 | 0.015 | 0.013 | 0.013 | 0.013 |
| Water to 100% | | | | | | | | | | |

[1]Ethyl 1-(2,4-dichlorophenyl)-5-trichloromethyl-(1H)-1,2,4-triazole-3-carboxylate
® Darvan No. 3 is the sodium salt of a polymeric benzoylalkylbulfonic acid

TABLE II

Biological comparison experiments

| | Herbicidal action against wild oats | |
|---|---|---|
| Tank mix of fenoxaprop-P-ethyl + isoproturon 500 g/l | (0.5 + 1 l/ha) | standard |
| Example 7 | (1.25 l/ha) | + (better than standard) |
| Example 9 | (1.25 l/ha) | ++ (significantly better than standard) |

We claim:

1. A suspoemulsion comprising 0.1 to 20% by weight of fenoxaprop-ethyl as a stereoisomer mixture or as the D(+)-isomer, 0.1 to 60% by weight of at least one herbicidal active compound from the phenyl urea series, 2 to 70% by weight of an aromatic solvent or solvent mixture, and 0.1 to 30% by weight of a surfactant combination of ethoxylated tristyrylphenol and ethoxylated sterically modified synthesis alcohol of average chain length $C_{13}$, each of which can be phosphated and neutralized with alkali or amine, wherein the ratio of ethoxylated tristyrylphenol and ethoxylated sterically modified synthesis alcohol is 25:1 to 1:35.

2. A suspoemulsion as claimed in claim 1 comprising 0.2 to 10% by weight of fenoxaprop-ethyl as a stereoisomer mixture or as the D(+)-isomer, 1 to 45% by weight of at least one herbicidal active compound from the phenyl urea series, 3 to 50% by weight of an aromatic solvent or solvent mixture, and 0.5 to 20% by weight of the surfactant combination, wherein the ratio of ethoxylated tristyrylphenol and ethoxylated sterically modified synthesis alcohol is 4:1 to 1:8.

3. A suspoemulsion as claimed in claim 2 wherein the herbicidal compound is isoproturon.

4. A formulation as claimed in claim 1, which comprises a solvent mixture of an aromatic solvent and a naturally occurring oil of animal or vegetable origin.

5. A formulation as claimed in claim 1, which additionally comprises another surfactant and/or customary auxiliaries from the series comprising wetting agents, dispersing agents, foam suppressants, thickeners, preservatives and antifreeze agents.

6. A formulation as claimed in claim 1, comprising isoproturon.

7. A method of combating undesirable plant growth, in which an amount of a formulation as claimed in claim 2 sufficient for combating the growth is applied to plants, plant seeds or the cultivation area.

8. A formulation as claimed in claim 1, which comprises a solvent mixture of an aromatic solvent and a naturally occurring oil of animal or vegetable origin.

9. A formulation as claimed in claim 1, which additionally comprises another surfactant and/or customary auxiliaries from the series comprising wetting agents, dispersing agents, foam suppressants, thickeners, preservatives and antifreeze agents.

10. A formulation as claimed in claim 2, comprising isoproturon.

11. A method of combating undesirable plant growth, in which an amount of a formulation as claimed in claim 1 sufficient for combating the growth is applied to plants, plant seeds or the cultivation area.

12. A composition consisting essentially of 0.1 to 20% by weight of fenoxaprop-ethyl as a stereoisomer mixture or as the D(+)-isomer, 0.1 to 60% by weight of at least one herbicidal active compound from the 2 to 70% by weight of an aromatic solvent or solvent mixture, and 0.1 to 30% by weight of a surfactant combination of ethoxylated tristyrylphenol and ethoxylated sterically modified synthesis alcohol of average chain length $C_{13}$, each of which can be phosphated and neutralized with alkali or amine, wherein the ratio of ethoxylated tristyrylphenol and ethoxylated sterically modified synthesis alcohol is 25:1 to 1:35; and, the composition is a suspoemulsion.

* * * * *